(12) United States Patent
Eisner et al.

(10) Patent No.: US 10,748,270 B2
(45) Date of Patent: Aug. 18, 2020

(54) APPARATUS FOR CARRYING OUT A NON-DESTRUCTIVE INSPECTION ON WOODEN BOARDS OR SIMILAR OBJECTS

(71) Applicant: MICROTEC S.R.L., Bressanone (Bolzano) (IT)

(72) Inventors: Egon Eisner, Friesach (AT); Herbert Zambra, Lienz (AT); Konrad Tschurtschenthaler, Castelrotto (IT); Johann Thaler, Bressanone (IT)

(73) Assignee: MICROTEC S.R.L., Bressanone (IT)

( * ) Notice: Subject to any disclaimer, the term of this patent is extended or adjusted under 35 U.S.C. 154(b) by 0 days.

(21) Appl. No.: 15/458,422

(22) Filed: Mar. 14, 2017

(65) Prior Publication Data

US 2017/0270657 A1    Sep. 21, 2017

(30) Foreign Application Priority Data

Mar. 16, 2016   (IT) .......................... 102016000027793

(51) Int. Cl.
*G06T 7/00* (2017.01)
*G01N 33/46* (2006.01)
(Continued)

(52) U.S. Cl.
CPC .......... *G06T 7/0004* (2013.01); *G01N 23/046* (2013.01); *G01N 23/083* (2013.01);
(Continued)

(58) Field of Classification Search
CPC ....... G01N 2223/619; G01N 2223/643; G01N 23/046; G01N 23/083; G01N 33/46;
(Continued)

(56) References Cited

U.S. PATENT DOCUMENTS

| 3,967,721 A | 7/1976 | Rhoden |
| 5,499,112 A * | 3/1996 | Kawai ................. G02B 6/0001 358/475 |

(Continued)

FOREIGN PATENT DOCUMENTS

| AT | 507081 | 2/2010 | |
| DE | 4239692 A1 * | 6/1993 | ......... G01N 21/8986 |

(Continued)

OTHER PUBLICATIONS

Machine translation, JP 2011-121781 A.*

(Continued)

*Primary Examiner* — Michelle M Entezari
(74) *Attorney, Agent, or Firm* — Pearne & Gordon LLP (57) ABSTRACT

This invention relates to an apparatus (1) for carrying out a non-destructive inspection on a wooden board (9) or a similar object. The apparatus (1) comprises a movement system (3) comprising at least two chains or belts (32) that are at a distance from one another and substantially parallel to each other. The chains or belts (32) are slidable parallel to a movement path (30) and are and intended to support the wooden board (9). The apparatus (1) also comprises a non-destructive inspection station (2) that is positioned on the movement path (30), for carrying out a non-destructive inspection on the wooden board (9) that is supported by the chains or belts (32). The non-destructive inspection station (2) comprises at least one operating component (22) that is positioned on the same side as the chains or belts (32) and emits or receives a signal or an image, with an emission or reception field (220) that faces towards a region between two chains or belts (32). Each chain or belt (32) comprises an elongate flexible body (320) and at least one rest element (36) that is positioned on the elongate flexible body (320). The at least one rest element (36) projects upwards from the elongate flexible body (320) and has a top face (361) with a (Continued)

width (L36) that is less than the width (L32) of the elongate flexible body (320). The top faces (361) are intended to provide a surface on which the wooden board (9) can rest, so that the wooden board is kept at a distance from the elongate flexible body (320) of each chain or belt (32).

33 Claims, 4 Drawing Sheets (51) Int. Cl.
G01N 23/18 (2018.01)
G01N 23/046 (2018.01)
G01N 23/083 (2018.01)
B65G 17/00 (2006.01)

(52) U.S. Cl.
CPC .............. *G01N 23/18* (2013.01); *G01N 33/46* (2013.01); *B65G 17/002* (2013.01); *G01N 2223/619* (2013.01); *G01N 2223/643* (2013.01); *G06T 2207/10072* (2013.01); *G06T 2207/10116* (2013.01)

(58) Field of Classification Search
CPC . G06T 2207/10072; G06T 2207/10116; G06T 7/0004
See application file for complete search history.

(56) References Cited

U.S. PATENT DOCUMENTS

| | | | | |
|---|---|---|---|---|
| 5,605,216 A * | 2/1997 | Raybon | ................... | B27B 31/04 144/357 |
| 6,031,567 A * | 2/2000 | Johnson | ............. | G01N 21/8986 348/130 |
| 6,054,712 A * | 4/2000 | Komardin | .............. | A61B 6/483 250/363.06 |
| 7,040,477 B2 | 5/2006 | Brixius et al. | | |
| 7,221,732 B1 * | 5/2007 | Annis | ................... | G01N 23/04 378/14 |
| 7,635,853 B1 * | 12/2009 | Shi | ......................... | B41J 11/009 250/559.01 |
| 7,731,020 B2 | 6/2010 | Bigler et al. | | |
| 7,740,799 B2 * | 6/2010 | Loda | ...................... | A23L 3/263 422/186.04 |
| 7,891,159 B2 * | 2/2011 | Iocco | ................... | B65B 31/024 53/432 |
| 7,926,359 B2 * | 4/2011 | Knispel | ................... | G01N 3/20 73/852 |
| 8,250,922 B2 | 8/2012 | Giudiceandrea | | |
| 8,553,838 B2 * | 10/2013 | Sommer | ................ | B07C 5/3427 378/45 |
| 8,794,423 B2 * | 8/2014 | Sasstamo | ................... | B07C 5/14 198/457.02 |
| 8,879,791 B2 * | 11/2014 | Drouin | ................. | G01N 23/046 378/57 |
| 2002/0067797 A1 * | 6/2002 | Safai | ........................ | A22B 5/00 378/54 |
| 2004/0168888 A1 | 9/2004 | Brixius et al. | | |
| 2004/0246473 A1 * | 12/2004 | Hermary | ............ | G01N 21/8986 356/237.1 |
| 2005/0097021 A1 * | 5/2005 | Behr | ....................... | G01N 21/85 705/36 R |
| 2007/0003009 A1 * | 1/2007 | Gray | ...................... | G01N 23/04 378/57 |
| 2008/0140248 A1 * | 6/2008 | Moore | ...................... | B07C 5/14 700/223 |
| 2008/0217141 A1 | 9/2008 | Bigler et al. | | |
| 2008/0292050 A1 * | 11/2008 | Goodenough | ......... | G01V 5/005 378/57 |
| 2010/0064810 A1 | 3/2010 | Giudiceandrea | | |
| 2011/0142201 A1 * | 6/2011 | Eberhard | ............. | G01V 5/0008 378/57 |
| 2013/0140147 A1 * | 6/2013 | Lasecki | ................ | B65G 17/064 198/851 |
| 2014/0083268 A1 * | 3/2014 | Rother | ..................... | B26D 5/20 83/52 |
| 2014/0163885 A1 * | 6/2014 | Clar | ......................... | G01V 9/00 702/5 |
| 2015/0369955 A1 * | 12/2015 | Al-Hoshani | ......... | G01V 5/0016 378/57 |
| 2016/0250665 A1 * | 9/2016 | Lampe | ..................... | B07C 5/02 209/587 |
| 2016/0349192 A1 * | 12/2016 | Yamakawa | .............. | A61B 6/02 |

FOREIGN PATENT DOCUMENTS

| | | |
|---|---|---|
| DE | 10064891 | 6/2002 |
| EP | 2166351 A1 | 3/2010 |
| JP | 2004323129 A * | 11/2004 |
| JP | 2011121781 A | 6/2011 |
| WO | 2008109748 | 9/2008 |

OTHER PUBLICATIONS

Machine translation JP 2004-323129 A.*
Machine translation AT 507 081 B1.*
Machine translation DE 10064891 A1.*
Machine translation of DE 4239692 A1 (Year: 1993).*

* cited by examiner

APPARATUS FOR CARRYING OUT A NON-DESTRUCTIVE INSPECTION ON WOODEN BOARDS OR SIMILAR OBJECTS

This invention relates in general to the sector of analysis of objects or components using non-destructive techniques and, specifically, it relates to an apparatus for carrying out a non-destructive inspection on wooden boards or similar objects.

In the sector there are prior art apparatuses for carrying out X-rays, tomographic scans, scans or visual inspections of wooden boards, for example so as to identify defects or to determine the orientation of the fibres.

In some prior art apparatuses, the wooden boards are moved by conveyor belts or chains that are parallel to each other. Each wooden board rests on two or more conveyor belts or chains, which therefore support the wooden board. A sliding movement of the conveyor belts or chains pulls the wooden boards along a movement path and, in particular, brings the wooden boards into an inspection station in which, depending on the type of apparatus, an X-ray, tomographic scan, a scan or inspection is carried out for each wooden board.

The inspection station usually comprises an operating component that is located below the wooden board, that is to say, on the same side as the conveyor belts or chains that support and move the wooden board. That operating component may, for example, be an X-ray emitter for taking X-rays or a tomography machine or a video camera for inspecting the lower face of the wooden board.

In that configuration of the inspection station, a disadvantage encountered is that the conveyor belts or chains cover the corresponding zones of the lower face of the wooden board that rests on them, preventing or interfering with the inspection of those zones. In other words, it is not possible to completely inspect the wooden board, because some zones of it are obscured, relative to the operating component, due to the conveyor belts or chains in contact with those zones.

To reduce the extent of this disadvantage, the use of very narrow, almost thread-like chains or belts was proposed, whose small width reduces the contact surface and, therefore, the extent of the obscured zones. However, width reduction acts to the detriment of the mechanical resistance of the chain or belt, consequently limiting the load of wooden boards that can be supported and moved. In light of that, the width cannot be reduced below a predetermined limit and, therefore, obscured zones having considerable dimensions remain. Moreover, due to the reduced mechanical resistance, that solution may result in a higher incidence of problems and faults during apparatus operation.

In this context the technical purpose which forms the basis of this invention is to provide an apparatus for non-destructive inspection that allows the above-mentioned disadvantages to be eliminated, or at least reduced, and/or that allows advantages compared with the prior art.

The technical purpose specified and the aims indicated are substantially achieved by an apparatus for carrying out a non-destructive inspection according to claim 1. Particular embodiments of this invention are defined in the corresponding dependent claims.

According to one aspect of an apparatus according to this invention, each chain or belt (or band) that supports and moves the wooden boards comprises, in addition to an elongate flexible body that extends along the movement path (like the prior art chains or belts), at least one rest element that is positioned on the elongate flexible body and is designed to receive a wooden board in such a way that the wooden board rests on it. Each rest element projects upwards from the elongate flexible body and has a top face on which the wooden board can rest. The width of the top face is less than the width of the elongate flexible body of the chain or belt.

Basically, the rest elements allow a reduction in the contact zone between the wooden board and the chains or belts that support it. In fact, said contact zones are limited to the top faces of the rest elements. At the same time, that reduction of the contact zone may be achieved without modifying the thickness of the chain or belt and, therefore, without reducing the mechanical resistance of the chain or belt.

In use, in the inspection station the rest elements hold the wooden board in a position at a distance from the elongate flexible body of each chain or belt. Thanks to the smaller width of the top face of the rest elements, the wooden board has one or more surface zones that face towards the elongate flexible body of a respective chain or belt and that are left uncovered, thereby being able to be included in the field of action or vision of the operating component of the inspection station.

In some embodiments, the rest elements are substantially wedge-shaped. In particular, they are prisms with a triangular or trapezoidal base. A shape with a trapezoidal base may be preferable to a shape with a triangular base, because it prevents the top face from being a sharp edge which could become damaged or could damage the wooden board.

In some embodiments, each rest element is made of at least two pieces and comprises a base piece, that is fixed to the elongate flexible body of the respective chain or belt, and a top piece that comprises the top face. The top piece is removably mounted on the base piece, in such a way that it can be substituted. That is useful for ensuring that wear and any damage caused by contact with the wooden boards only affects the top piece, which when necessary can easily be removed and substituted with a new top piece, without the need to substitute the entire rest element and/or to remove the base piece from the elongate flexible body.

In specific embodiments, each chain or belt comprises a plurality of rest elements, that are positioned one after another along the respective elongate flexible body.

Further features and the advantages of this invention are more apparent in the detailed description of its embodiments below. Reference will be made to the accompanying drawings, in which.

With reference to the accompanying figures, the numeral 1 denotes in its entirety an apparatus for carrying out a non-destructive inspection on a wooden board 9 or a similar object. It should be noticed that the accompanying figures are schematic illustrations of the apparatus 1, in which the parts are shown in a simplified way, with the aim of making it easy to understand what is described herein. Therefore, the accompanying figures do not include all of the components of the apparatus 1, are not drawn to scale and use functional blocks to denote the various components important for this description.

Hereinafter in this description, reference will be made to objects to be inspected that are wooden boards 9. However, it shall be understood that an apparatus 1 according to this invention may also be applied for non-destructive inspections of other objects that have a similar shape, such as planks, sheets made of any material, tiles, sheet metal. Moreover, the apparatus 1 could also be applied for wooden logs.

For example, in some embodiments, the non-destructive inspection is an X-ray or a tomographic scan, which allow the identification of defects in the structure of the wood by the use of X-rays. In other embodiments, the non-destructive inspection is a visual analysis carried out using video cameras to identify visible defects on the surfaces of the wooden board or to detect other features such as the orientation of the fibres of the wood. In yet other embodiments, the non-destructive inspection is a scan (for example, using microwaves) or another inspection that allows the measurement or detection of physical, morphological or structural characteristics of the wooden board.

The apparatus 1 comprises a supporting structure (not shown in detail in the figures), a non-destructive inspection station 2 and a movement system 3 for moving a wooden board 9 along a movement path 30 that is substantially straight. In particular, the movement system 3 can simultaneously move a plurality of wooden boards 9, which are arranged one after another and pass through the non-destructive inspection station 2 one after another.

The movement system 3 comprises at least two chains or belts 32 that are at a distance from one another and substantially parallel to each other. For example, the distance between the two chains or belts 32 may be 50 cm.

The term belt also refers to a band or other similar member, made of a single piece or of multiple pieces that are joined together to form a substantially continuous member.

Basically, each chain or belt 32 comprises an elongate flexible body 320, that has structural continuity and extends at least partly parallel to the movement path 30.

In the case of a chain, that elongate flexible body 320 is formed by a plurality of links or rings 325, connected to each other one after another according to a structure that is known for example in the chain conveyors sector.

In the case of a belt, the elongate flexible body 320 is ribbon-like and may be made in a single piece or made of multiple pieces that are joined together, according to structures that are known for example in the conveyor belts sector.

In the embodiment illustrated in figures, there are three chains 32 which are coplanar. A central chain is interposed between the other two chains, in a position substantially equidistant from the latter two. Hereinafter in the description reference will be made to chains, although it shall be understood that what is described can also apply to belts or bands.

The chains 32 are intended to support the one or more wooden boards 9, that rest on the chains 32 during operation of the apparatus 1. A lower face of each wooden board 9 faces towards the chains 32 and is in contact with them. In turn, the chains 32 slidably rest on respective bars or guides that are part of the supporting structure of the apparatus 1. Those bars or guides, which are parallel to the movement path 30, support the chains 32 and transfer to the rest of the supporting structure the weight of the chains 32 and of the wooden boards 9 moved by the chains. The bars or guides are not shown in FIGS. 1 to 8. One of the bars or guides is shown only in FIGS. 9 to 11, in which it is labelled 31.

Figure 1:
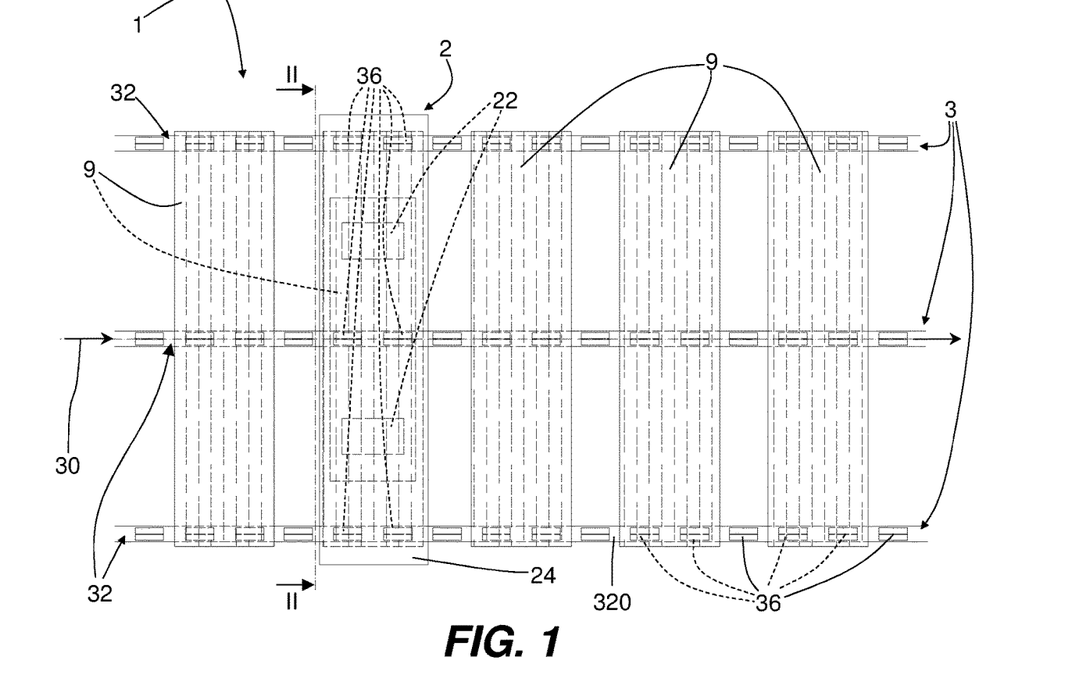
FIG. 1 is a schematic top view of an apparatus according to this invention, with a plurality of wooden boards.

In particular, as shown in FIG. 1, the wooden boards 9 are positioned transversally (or orthogonally) relative to the movement path 30. In other words, for each wooden board 9 the main direction of extension to which the largest dimension of the board 9 corresponds is transversal or orthogonal to the movement path 30.

The chains 32 are parallel to the movement path 30 and can slide along the movement path 30. That is to say, they are movable parallel to the latter. Therefore, the moving chains 32 pull with them the wooden boards 9 that rest on the chains 32 and, in particular, carry the wooden boards 9 through the non-destructive inspection station 2, which is located in an intermediate position along the movement path 30.

Specifically, the chains 32 are closed in a loop and are mounted on respective end pulleys (not illustrated in the figures), which keep the chains 32 appropriately tensioned. For example, as shown in a simplified way in FIG. 2, each chain 32 closed in a loop has an upper stretch 321 that supports the wooden boards 9 (also resting on a respective bar or guides 31) and a lower stretch 322 that performs a return stroke. At least one pulley for each chain 32 is motor-driven and, during operation, drives the rotation of the respective looped chain 32 in such a way that the upper stretch 321 slides in the direction of feed along the movement path 30. In use, the chains 32 behave like chain conveyors or conveyor belts.

The non-destructive inspection station 2 is designed to carry out the non-destructive inspection on a wooden board 9 while the latter is supported by the chains 32 and passes through the non-destructive inspection station 2. Therefore, it is an inspection station that operates in the line, without the need for an additional movement to pick up the wooden board 9 from the movement path 30.

The non-destructive inspection station 2 comprises at least one operating component 22 that, relative to the wooden board 9 located in the non-destructive inspection station 2, is positioned on the same side as the chains 32. In other words, the operating component 22 is also below the wooden board 9, as are the chains 32. Relative to the non-destructive inspection to be carried out, the operating component 22 is intended to emit or receive a signal or an image.

In particular, the operating component 22 has an emission or reception field 220 that faces towards a region that is delimited by a first chain 32 and by a second chain 32. In use, the operating component 22 is positioned in a region between two chains 32, in particular equidistant from them, and during operation of the emission or reception field 220 faces towards the lower face of the wooden board 9. Because of the spatial limitation due to the presence of the chains 32, the portion of lower face struck by the emission or reception field 220 is substantially that between the rests on the two chains 32.

The emission or reception field 220 of the operating component 22 has a respective angular amplitude α22.

Figure 2:
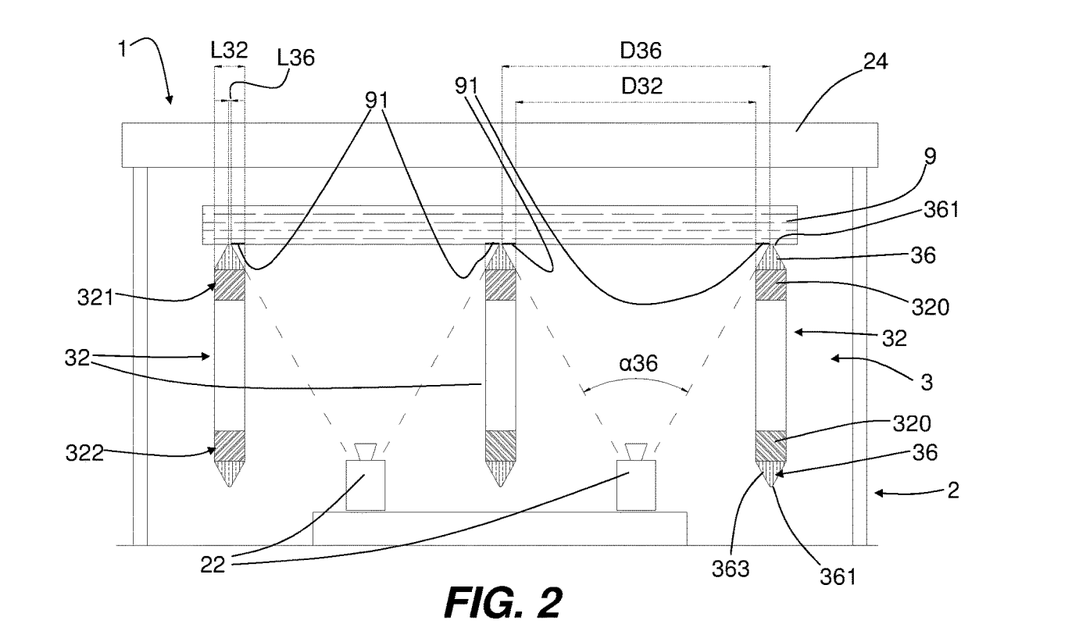
FIG. 2 is a cross-section of the apparatus of FIG. 1, according to a cross-section line II-II.
Figure 3:
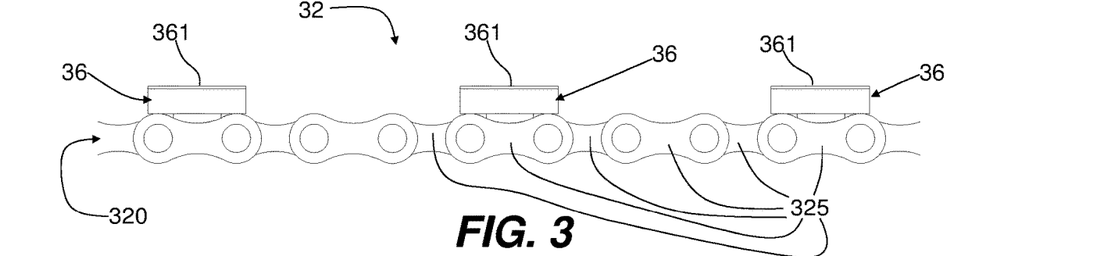
FIG. 3 is a side view of an embodiment of a component of the apparatus of FIG. 1.
Figure 4:
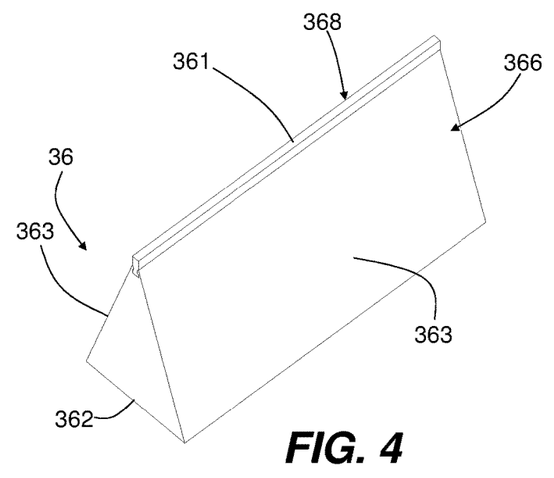
FIG. 4 is an axonometric view of an element of the component of FIG. 3.
Figure 5:
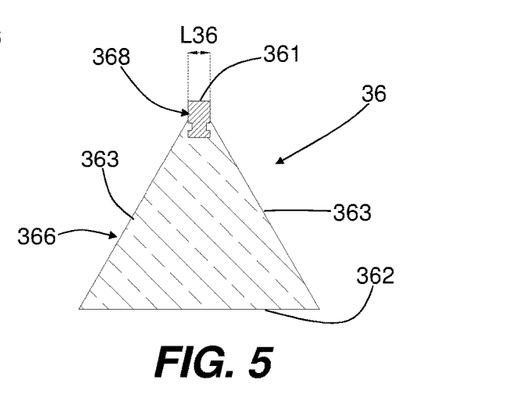
FIG. 5 is a cross-section of the element of FIG. 4.
Figure 6:
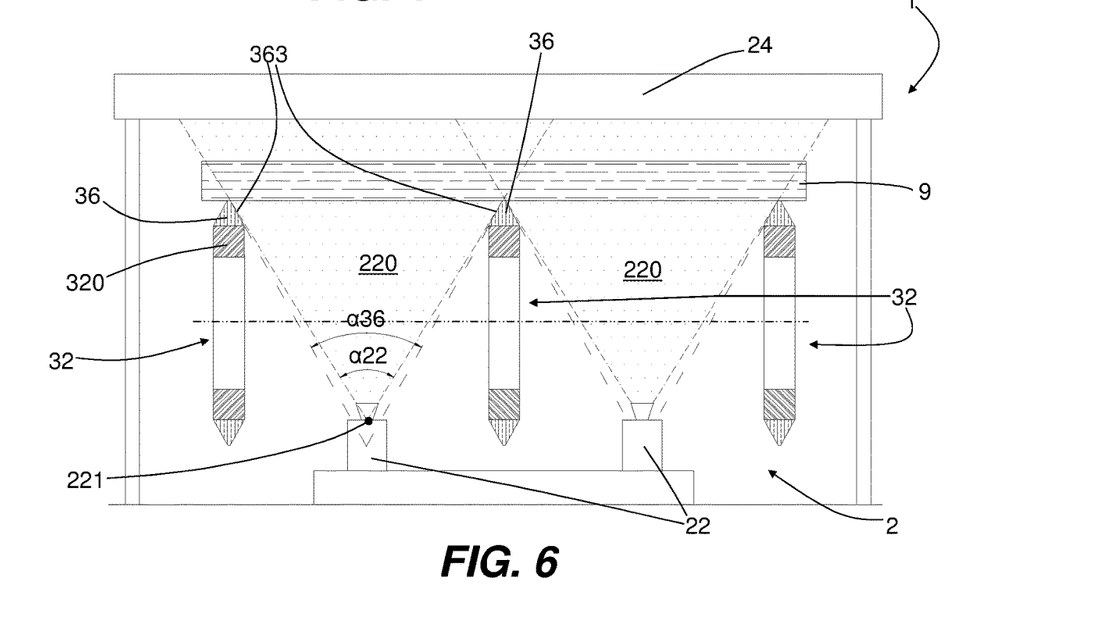
FIG. 6 illustrates, in a view corresponding to FIG. 2, an aspect of operation of a first embodiment of an apparatus according to this invention.

In some embodiments in which the apparatus 1 is used for taking an X-ray of the wooden board 9, the non-destructive inspection station 2 is a radiographic device and the operating component 22 is an X-ray emitter. In that case, the non-destructive inspection station 2 may comprise at least one other operating component 24 that is an X-ray receiver, said receiver 24 being positioned on the opposite side of the wooden board 9 for receiving the X-rays emitted by the emitter 22 that have passed through the wooden board 9 (FIGS. 1, 2 and 6). In alternative embodiments in which the operating component 22 is an X-ray emitter, the apparatus 1 is used to perform a tomographic scan of the wooden board 9 and the non-destructive inspection station 2 is a tomography machine.

In some possible alternative embodiments, the two operating components 22, 24 could be positioned the other way around, that is to say, the operating component 22 below the wooden board 9 may be a signal receiver and the other operating component 24 above the wooden board 9 may be a signal emitter, in such a way that the signals emitted by the operating component 24 are direct towards the receiver 22 below and pass through the wooden board 9. Those signals could be X-rays, microwaves or other suitable signals.

Figure 7:
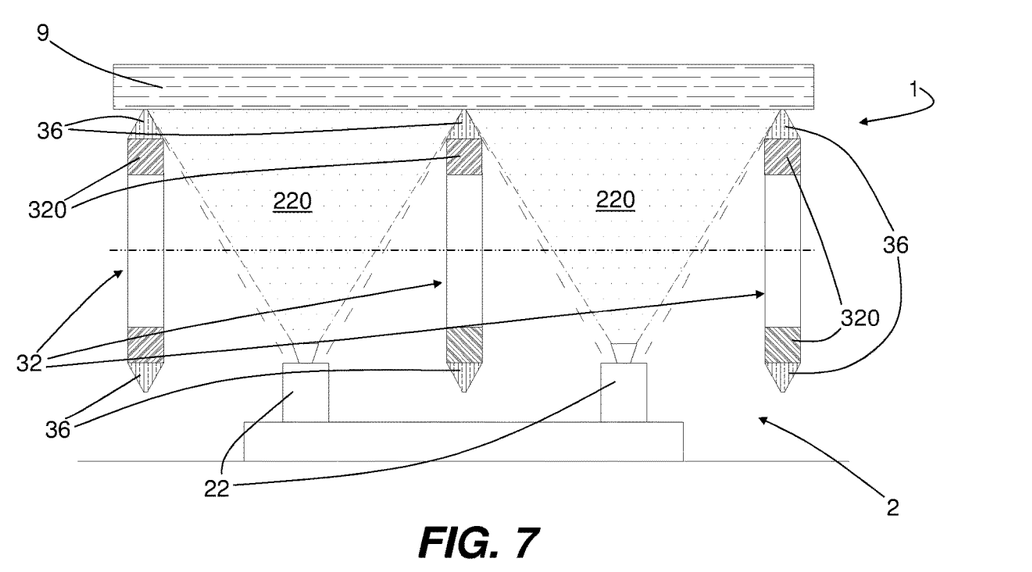
FIG. 7 illustrates, in a view corresponding to FIG. 2, an aspect of operation of a second embodiment of an apparatus according to this invention.

In other embodiments, in which the apparatus 1 is used for performing a visual analysis of the wooden board 9, the non-destructive inspection station 2 is a vision system and the operating component 22 is a video camera, intended to receive an image of the lower face of the wooden board 9 (FIG. 7).

In the embodiment illustrated, in which there are three chains 32, the non-destructive inspection station 2 comprises two operating components 22, which are identical to each other. With reference to FIG. 2, a first operating component 22 is positioned in such a way that it faces towards a region delimited by the left-hand chain 32 and the central chain 32, a second operating component 22 is positioned in such a way that it faces towards a region delimited by the central chain 32 and the right-hand chain 32. In that way, the length of the wooden board 9 is divided into a plurality of regions, each of which is within the emission or reception field 220 (that is to say, within the inspection field) of a respective operating component 22.

In other embodiments, there may be more than three chains 32 and more than two operating components 22, which are arranged in such a way that each operating component 22 faces towards a respective region delimited by a respective pair of chains 32.

According to one aspect of this invention, each chain 32 comprises, in addition to the elongate flexible body 320, a plurality of rest elements 36 that are positioned one after another along the elongate flexible body 320 and are designed to receive the wooden board 9 in such a way that it rests on them. Each rest element 36 projects upwards from the elongate flexible body 320 and has a top face 361 intended to support the wooden board 9 resting on it. In use, the rest elements 36 are spacers designed to keep the wooden board 9 raised relative to the elongate flexible body 320 of the respective chain 32.

The top face 361 of each rest element 36 has a with L36 that is less than the width L32 of the elongate flexible body 320 of the respective chain 32. Those widths are measured along a line transversal or orthogonal to the direction of feed 30, in particular along the main line of extension of the wooden boards 9 conveyed by the movement system 3.

For example, the width L36 may be approximately several millimetres. During apparatus 1 operation, the wooden board 9 located in the non destructive inspection station 2 rests on respective rest elements 36. Since the top face 361 of each rest element 36 is narrower than the elongate flexible body 320, the lower face of the wooden board 9 has respective surface zones that face towards the elongate flexible body 320 below and are within the emission or reception field 220 of the operating component 22. Those surface zones, which are both at the side of the rest elements 36 and between two rest elements 36 on the same chain 32, are clearer in FIG. 2, where they are labelled 91. FIGS. 6 and 7 show that even those surface zones 91 are visible to or detectable by the operating component 22, since they are within the field 220 and are not obscured by the chains 32.

Basically, the rest elements 36 allow a reduction in the contact surface between chains 32 and wooden board 9 without reducing the width of the structure of the chains 32 and, therefore, without altering the mechanical resistance of the chains. Moreover, by spacing the wooden board 9 from the elongate flexible bodes 320 and exploiting the angular amplitude of the emission or reception field 220, the rest elements 36 allow zones obscured by the chains 32 to be substantially eliminated.

Figure 8:
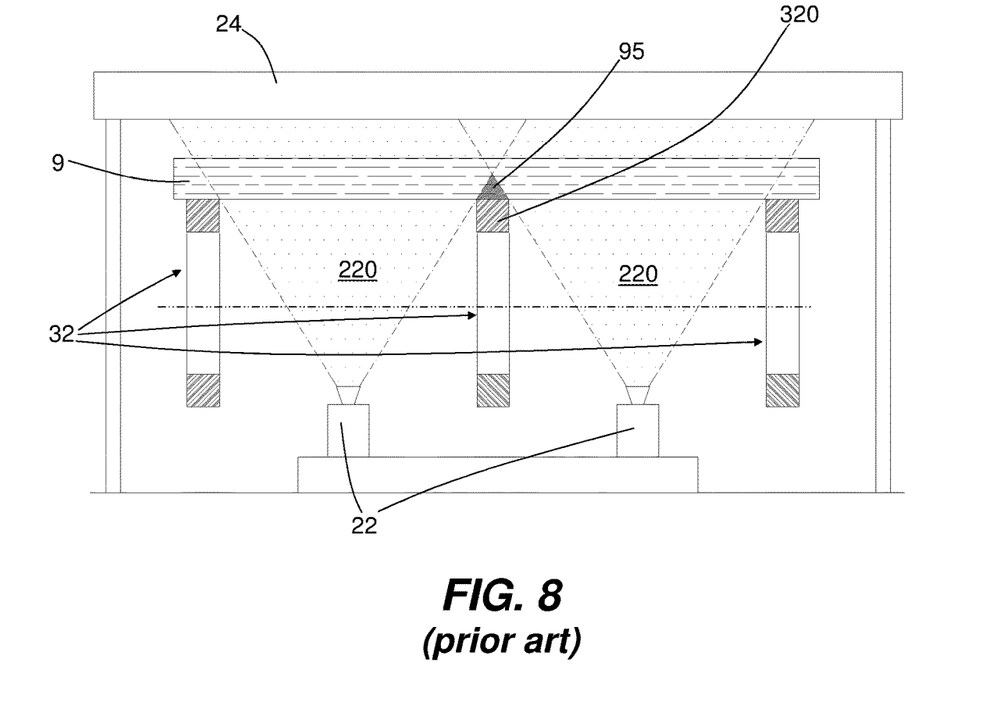
FIG. 8 illustrates, in a view corresponding to FIG. 2, an aspect of operation of a prior art apparatus.

To better appreciate this aspect, consider FIG. 8, which shows a corresponding prior art apparatus, where the chains are without rest elements 36 and the wooden board 9 rests directly on the elongate flexible bodies 320 of the chains. For example, above the central chain there is an obscured zone 95 that, in the case of an X-ray or a tomographic scan, cannot be reached by the X-rays and, therefore, cannot be inspected. FIG. 6 shows that said obscured zone 95 is substantially eliminated for an apparatus 1 according to this invention, thanks to the fact that the rest elements 36 make even the surface zones 91 accessible.

Since defects with dimensions of less than 5 mm in the wooden board 9 are usually not very important for the purposes of non-destructive inspection, the small obscured zones caused by the top faces 361 in contact with the wooden board 9 are effectively negligible, in particular if a width L36 of approximately several millimetres is selected.

It should also be noticed that the lateral edges of the wooden boards 9 are usually of little interest, since those edges can be sawn during subsequent processing operations to adapt the board 9 to the required dimensions.

Therefore, any obscured zones that remain on the outside of the right hand chain 32 and the left-hand chain 32 do not cause any particular disadvantages. In any case, it should be noticed that, compared with the prior art, the use of rest elements 36 also allows a reduction in the extent of those outer obscured zones.

Considering two chains 32 between which the emission or reception field 220 of an operating component 22 is located, the distance D36 between the top face 361 of a rest element 36 of the first chain 32 and the top face 361 of an opposite rest element 36 of the second chain 32 is greater than the distance D32 between the elongate flexible bodies 320 of the first chain and of the second chain. In use, the top face 361 is recessed relative to the side of the respective chain 32.

In the embodiment illustrated, each rest element 36 is substantially wedge-shaped. In particular, it is a wedge-shaped prism with a cross-section that substantially has the shape of a triangle or a trapezium (FIGS. 4 and 5), even more particularly, having the shape of an isosceles triangle or an isosceles trapezium. The width of the top face 361 is less than the width of a bottom face 362 opposite to the top face 361. Moreover, at least one longitudinal lateral face 363 (parallel to the direction of movement 30) is inclined.

In the embodiment with a triangular cross-section, the top face 361 is substantially reduced to an edge. In some cases that solution may not be recommended, due to the possibility of damage to the wooden board 9 or greater wear of the rest 36. Therefore, an embodiment with a trapezium-shaped cross-section with the smaller base at the top (for example, having a width of several millimetres) may be preferable.

In the non-destructive inspection station 2, the longitudinal lateral face 363 of each rest element 36 of the first chain 32 and the longitudinal lateral face 363 of an opposite rest element 36 of the second chain 32 are inclined relative to each other in such a way that they converge towards the operating component 22. In particular, as shown in FIGS. 2 and 6, those longitudinal lateral faces 363 define an angle $\alpha 36$ between them.

In order to minimise the obscured zones, the operating component 22 is positioned in such a way that the vertex 221 of its emission or reception field 220 is in a convex angular sector defined by the convergence of the longitudinal lateral faces 363 (as shown in FIG. 6). Moreover, the angle $\alpha 36$ of convergence between the longitudinal lateral faces 363 has an amplitude which is less than the angular amplitude of the emission or reception field 220 of the operating component 22.

In the embodiment illustrated in the figures, each rest element 36 comprises a base piece 366, that is fixed to the elongate flexible body 320 of the respective chain 32, and a top piece 368 that comprises the top face 361. The top piece 368 is removably mounted on the base piece 366, for example, it can be inserted in and remove from a suitable seat, in such a way that it can be substituted. In use, the top piece 368, which for example is made of rubber, is a small pad occupying the tip region of the rest element 36 and is intended to make contact with the wooden boards 9. When the top piece 368 is worn or damaged, it can be substituted with a new one, without the need to substitute the entire rest element 36.

The rest elements 36 may for example be made of plastic material, metal, wood, rubber of another material with suitable mechanical resistance. The rest elements 36 can be fixed to the respective elongate flexible body 320 using methods that are appropriate in each case. For example, they may be glued, wedged in, clamped, fixed with screws, nails or staples. In other alternative embodiments, the rest elements 36 may be made in one piece with the respective elongate flexible body 320, for example a belt 32 is made in one piece incorporating an elongate flexible body 320 and rest elements 36 that project from the latter.

For an elongate flexible body 320 formed by a plurality of links 325, as in the case of a chain 32, each rest element 36 may be fixed to a respective link 325. In one embodiment, each link 325 is equipped with a rest element 36. In other embodiments, the rest elements 36 are distributed further apart, that is to say, links 325 without a rest element 36 are interposed between links 325 equipped with respective rest elements 36, as shown for example in FIG. 3.

Figure 9:
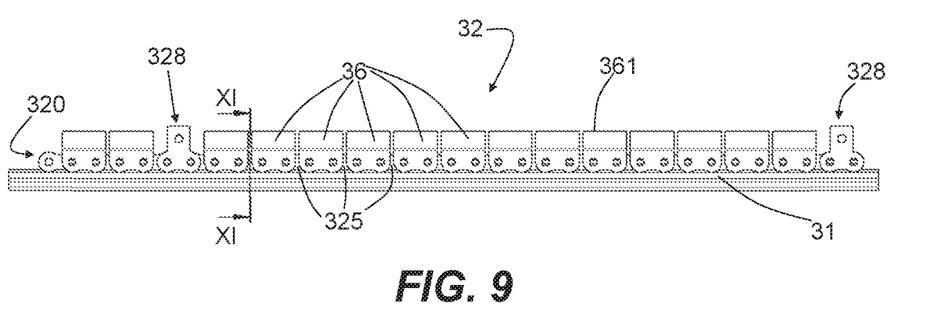
FIG. 9 is a side view of an alternative embodiment of the component of FIG. 3.
Figure 10:
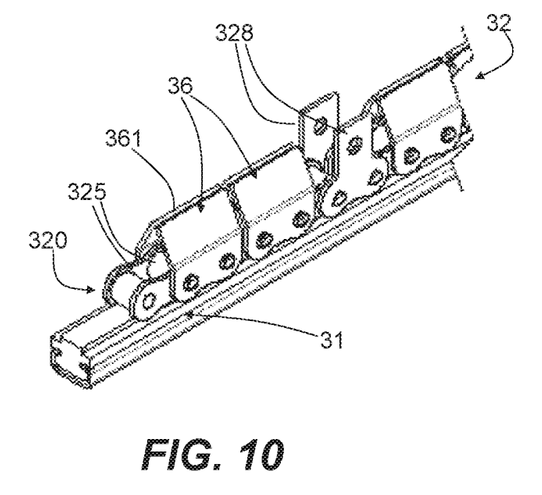
FIG. 10 is a perspective view of a portion of the component of FIG. 9.
Figure 11:
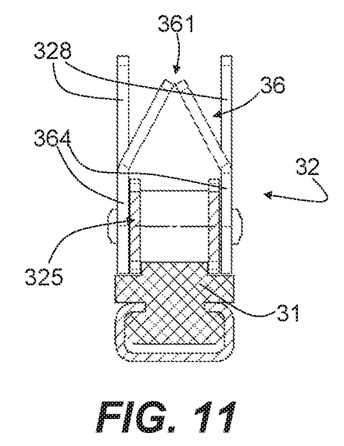
FIG. 11 is a cross-section, according to a cross-section line XI-XI, of the component of FIG. 9.

One alternative embodiment is shown in FIGS. 9 to 11, in which each rest element 36 comprises two plates 364 (for example made of sheet metal) which are fixed to the sides of the respective link 325 of the chain 32 and bent in such a way that they converge towards the top, so as to constitute said wedge shape and a top face 361 on which a wooden board 9 can rest. That alternative embodiment may be suitable in particular for wooden boards 9 that have not been planed.

For example, the alternative embodiment shown in FIGS. 9 to 11 has a rest element 36 for each link 325 of the chain 32, except several links that have pushing elements 328 projecting beyond the surface formed by the top faces 361. Those links with projecting pushing elements 328 are regularly spaced from one another and the projecting pushing elements 328 are intended to be inserted between consecutive wooden boards 9 on the chains 32, so as to push the wooden boards 9 forward and prevent the wooden boards 9 from being able to slide relative to the chains 32.

Pushing elements 328, that project from the surface formed by the tops of the rest elements 36, may also be present in the other embodiments of the subject matter of this invention. If necessary, those pushing elements 328 may be made in a different way, provided that they still fulfil the same function.

In FIGS. 9 to 11 it should also be noticed that each bar or guide 31 may have approximately the same width as the elongate flexible body 320 of the respective chain 32, so as to avoid creating any obscured zone on the wooden board 9.

Figure 12:
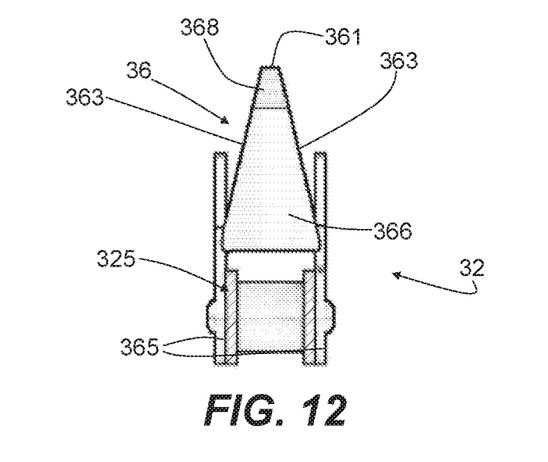
FIG. 12 is a cross-section of another alternative embodiment of the component of FIG. 3.

Another alternative embodiment is shown in FIG. 12, which corresponds to the cross-section of FIG. 11, but in which the bar or guide 31 is not shown. In this alternative embodiment, which is particularly suitable for planed wooden boards 9, the rest element 36 has a wedge-like prismatic shape (for example it is made of rubber) and is mounted on plates 365 fixed to the sides of the respective link 325 of the chain 32. This rest element 36 can also be made in two pieces (base piece 366 and top piece 368), similarly to what is described above.

For a ribbon-like elongate flexible body 320, as in the case of a conveyor belt or band, the respective rest elements 36 are fixed on the ribbon-like elongate flexible body, suitably spaced from each other.

In a further alternative embodiment, each chain or belt 32 may be equipped with only one rest element 36, which extends along the entire length of the elongate flexible body 320 of the chain or belt 32. In particular, the single rest element 36 may be made in one piece with the respective elongate flexible body 320. For example, a belt 32 (for example made of rubber) may have a pointed shape along its entire length, that pointed shape forming the rest element 36.

The invention described above may be modified and adapted in several ways without thereby departing from the scope of the appended claims.

All details may be substituted with other technically equivalent elements and the materials used, as well as the shapes and dimensions of the various components, may vary according to requirements.

The invention claimed is:

1. An apparatus (1) for carrying out a non-destructive inspection on a wooden board (9) or a similar object, comprising:
    a movement system (3) for moving a wooden board (9) or a similar object along a movement path (30), the movement system (3) comprising at least two chains or belts (32) that are at a distance from one another and substantially parallel to each other, the at least two chains or belts (32) being slidable parallel to the movement path (30) and intended to support said wooden board (9) or similar object;
    a non-destructive inspection station (2) that is positioned at an intermediate position of the movement path (30), the non-destructive inspection station (2) being designed to carry out a non-destructive inspection on a wooden board (9) or similar object that, during operation, is supported by the at least two chains or belts (32) and passes through the non-destructive inspection station (2), the at least two chains or belts (32) being present in the non-destructive inspection station (2) so as to support the wooden board (9) or similar object while the non-destructive inspection is carried out;

wherein the non-destructive inspection station (2) comprises at least one operating component (22) that, relative to the wooden board (9) or similar object in the non-destructive inspection station (2), is positioned on the same side as the at least two chains or belts (32), wherein the operating component (22) ether (i) emits a signal and has an emission field (220) or (ii) receives an image and has a reception field (220), wherein the emission or reception field (220) faces towards a region delimited by a first chain or belt (32) and by a second chain or belt (32), the emission or reception field (220) having a respective angular amplitude (a22) and a vertex (221), the emission or reception field (220) converging towards the operating component (22) so that, relative to the wooden board (9) or similar object in the non-destructive inspection station (2), the vertex (221) of the emission or reception field (220) is on the same side as the at least one operating component (22), wherein each chain or belt (32) comprises an elongate flexible body (320) and at least one rest element (36) that is positioned on the elongate flexible body (320) and is designed to receive the wooden board (9) or similar object in such a way that the latter rests on it, the at least one rest element (36) projecting upwards from the elongate flexible body (320) and having a top face (361) on which the wooden board (9) or similar object can rest, the top face (361) having a width (L36) that is less than the width (L32) of the elongate flexible body (320), those widths being measured along a line transversal or orthogonal to the movement path (30) to which the at least two chains or belts (32) are slidable parallel, whereby, during carrying out of the non-destructive inspection, in the non-destructive inspection station (2) the wooden board (9) or similar object rests on the top face (361) of the at least one rest element (36) of the first chain or belt (32) and on the top face (361) of the at least one rest element (36) of the second chain or belt (32), said rest elements (36) holding the wooden board (9) or similar object in a position at a distance from the elongate flexible body (320) of each chain or belt (32), and, thanks to the width (L36) of the top face (361) being less than the width (L32) of the elongate flexible body (320), the wooden board (9) or similar object comprises, at each chain or belt (32), at least one surface zone (91) that is at a side of the at least one rest element (36) and faces towards the respective elongate flexible body (320), the operating component (22) being positioned in such a way that said at least one surface zone (91) is within the emission or reception field (220) of the operating component (22) and is not obscured, relative to the operating component (22), by the chain or belt (32) comprising the respective elongate flexible body (320), whereby, during carrying out of the non-destructive inspection, said at least one surface zone (91) is visible to or detectable by the operating component (22), wherein the at least one rest element (36) comprises at least one longitudinal lateral face (363) that is inclined, wherein in the non-destructive inspection station (2) the longitudinal lateral face (363) of the at least one rest element (36) of the first chain or belt (32) and the longitudinal lateral face (363) of an opposite rest element (36) of the second chain or belt (32) are inclined relative to each other in such a way that they converge with an angle (a36) that has an amplitude which is less than the angular amplitude (a22) of the emission or reception field (220) of the operating component (22), the vertex (221) of the emission or reception field (220) being located in a convex angular sector defined by the convergence of the inclined longitudinal lateral faces (363).

2. The apparatus (1) according to claim 1, wherein in the non-destructive inspection station (2) the distance (D36) between the top face (361) of the at least one rest element (36) of the first chain or belt (32) and the top face (361) of an opposite rest element (36) of the second chain or belt (32) is greater than the distance (D32) between the elongate flexible bodies (320) of the first chain or belt (32) and of the second chain or belt (32).

3. The apparatus (1) according to claim 1, wherein the at least one rest element (36) is substantially wedge-shaped, in such a way that the top face (361) has a width that is less than a bottom face (362) opposite to the top face (361).

4. The apparatus (1) according to claim 1, wherein the at least one rest element (36) has a cross-section that substantially has the shape of a triangle or a trapezium, in particular having the shape of an isosceles triangle or an isosceles trapezium.

5. The apparatus (1) according to claim 1, wherein the at least one rest element (36) comprises a base piece (366) and a top piece (368) that comprises said top face (361), the top piece (368) being removably mounted on the base piece (366), in such a way that it can be substituted.

6. The apparatus (1) according to claim 1, wherein the at least one rest element of each chain or belt (32) extends along the entire length of the respective elongate flexible body (320).

7. The apparatus (1) according to claim 1, wherein each chain or belt (32) comprises a plurality of rest elements (36) that are positioned one after another along the respective elongate flexible body (320).

8. The apparatus (1) according to claim 7, wherein the elongate flexible body (320) of each chain or belt (32) is formed by a plurality of links (325) and each rest element (36) is fixed to a respective link (325).

9. The apparatus (1) according to claim 1, wherein the elongate flexible body (320) of each chain or belt (32) is ribbon-like and the respective at least one rest element (36) is fixed on the ribbon-like elongate flexible body (320), said at least two chains or belts (32) being conveyor belts.

10. The apparatus (1) according to claim 1, comprising at least three of said chains or belts (32) and at least two of said operating components (22), wherein each operating component (22) faces towards a respective region that is delimited by a respective pair of chains or belts (32).

11. The apparatus (1) according to claim 1, intended to carry out a non-destructive inspection on wooden boards (9) that are positioned transversally or orthogonally relative to the movement path (30), each wooden board (9) having a main direction of extension to which the largest dimension of the wooden board (9) corresponds, the main direction of extension being transversal or orthogonal to the movement path (30).

12. The apparatus (1) according to claim 1, wherein said non-destructive inspection is an X-ray or a tomographic scan, said non-destructive inspection station (2) being an X-ray device or a tomography machine and said operating component (22) being an X-ray emitter.

13. The apparatus (1) according to claim 1, wherein said non-destructive inspection is a visual analysis, said non-destructive inspection station (2) being a vision system and said operating component (22) being a video camera receiving an image of a lower face of the wooden board (9).

14. The apparatus (1) according to claim 2, wherein the at least one rest element (36) is substantially wedge-shaped, in such a way that the top face (361) has a width that is less than a bottom face (362) opposite to the top face (361) and that at least one longitudinal lateral face (363) is inclined.

15. The apparatus (1) according to claim 2, wherein the at least one rest element (36) has a cross-section that substantially has the shape of a triangle or a trapezium, in particular having the shape of an isosceles triangle or an isosceles trapezium.

16. The apparatus (1) according to claim 3, wherein the at least one rest element (36) has a cross-section that substantially has the shape of a triangle or a trapezium, in particular having the shape of an isosceles triangle or an isosceles trapezium.

17. The apparatus (1) according to claim 2, wherein the at least one rest element (36) comprises a base piece (366) and a top piece (368) that comprises said top face (361), the top piece (368) being removably mounted on the base piece (366), in such a way that it can be substituted.

18. The apparatus (1) according to claim 4, wherein the at least one rest element (36) comprises a base piece (366) and a top piece (368) that comprises said top face (361), the top piece (368) being removably mounted on the base piece (366), in such a way that it can be substituted.

19. The apparatus (1) according to claim 2, wherein the at least one rest element of each chain or belt (32) extends along the entire length of the respective elongate flexible body (320).

20. The apparatus (1) according to claim 4, wherein the at least one rest element of each chain or belt (32) extends along the entire length of the respective elongate flexible body (320).

21. The apparatus (1) according to claim 5, wherein the at least one rest element of each chain or belt (32) extends along the entire length of the respective elongate flexible body (320).

22. The apparatus (1) according to claim 2, wherein each chain or belt (32) comprises a plurality of rest elements (36) that are positioned one after another along the respective elongate flexible body (320).

23. The apparatus (1) according to claim 4, wherein each chain or belt (32) comprises a plurality of rest elements (36) that are positioned one after another along the respective elongate flexible body (320).

24. The apparatus (1) according to claim 2, wherein the elongate flexible body (320) of each chain or belt (32) is ribbon-like and the respective at least one rest element (36) is fixed on the ribbon-like elongate flexible body (320), said at least two chains or belts (32) being conveyor belts.

25. The apparatus (1) according to claim 4, wherein the elongate flexible body (320) of each chain or belt (32) is ribbon-like and the respective at least one rest element (36) is fixed on the ribbon-like elongate flexible body (320), said at least two chains or belts (32) being conveyor belts.

26. The apparatus (1) according to claim 2, wherein said non-destructive inspection is an X-ray or a tomographic scan, said non-destructive inspection station (2) being an X-ray device or a tomography machine and said operating component (22) being an X-ray emitter.

27. The apparatus (1) according to claim 4, wherein said non-destructive inspection is an X-ray or a tomographic scan, said non-destructive inspection station (2) being an X-ray device or a tomography machine and said operating component (22) being an X-ray emitter.

28. The apparatus (1) according to claim 5, wherein said non-destructive inspection is an X-ray or a tomographic scan, said non-destructive inspection station (2) being an X-ray device or a tomography machine and said operating component (22) being an X-ray emitter.

29. The apparatus (1) according to claim 2, wherein said non-destructive inspection is a visual analysis, said non-destructive inspection station (2) being a vision system and said operating component (22) being a video camera receiving an image of a lower face of the wooden board (9).

30. The apparatus (1) according to claim 4, wherein said non-destructive inspection is a visual analysis, said non-destructive inspection station (2) being a vision system and said operating component (22) being a video camera receiving an image of a lower face of the wooden board (9).

31. The apparatus (1) according to claim 5, wherein said non-destructive inspection is a visual analysis, said non-destructive inspection station (2) being a vision system and said operating component (22) being a video camera receiving an image of a lower face of the wooden board (9).

32. The apparatus (1) according to claim 9, wherein said non-destructive inspection is a visual analysis, said non-destructive inspection station (2) being a vision system and said operating component (22) being a video camera receiving an image of a lower face of the wooden board (9).

33. The apparatus (1) according to claim 11, wherein said non-destructive inspection is a visual analysis, said non-destructive inspection station (2) being a vision system and said operating component (22) being a video camera receiving an image of a lower face of the wooden board (9).

* * * * *

UNITED STATES PATENT AND TRADEMARK OFFICE
CERTIFICATE OF CORRECTION

PATENT NO. : 10,748,270 B2  
APPLICATION NO. : 15/458422  
DATED : August 18, 2020  
INVENTOR(S) : Egon Eisner et al.

Page 1 of 1

It is certified that error appears in the above-identified patent and that said Letters Patent is hereby corrected as shown below:

In the Claims

In Column 9, Line 14, please change "(22) ether (i) emits a" to -- (22) either (i) emits a --

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*